United States Patent [19]

Grayson

[11] 4,095,596

[45] Jun. 20, 1978

[54] NASAL INHALER

[75] Inventor: Michael A. Grayson, Wayne, Pa.

[73] Assignee: SmithKline Corporation, Philadelphia, Pa.

[21] Appl. No.: 745,082

[22] Filed: Nov. 26, 1976

[51] Int. Cl.[2] .............................................. A61M 15/08

[52] U.S. Cl. ..................................... 128/198; 128/206

[58] Field of Search ............... 128/196, 197, 198, 199, 128/200, 201, 206, 207, 208, 266

[56] References Cited

U.S. PATENT DOCUMENTS

| | | | |
|---|---|---|---|
| 2,395,109 | 2/1946 | Fonda | 128/200 |
| 2,549,303 | 4/1951 | Friden | 128/206 |
| 2,705,007 | 3/1955 | Gerber | 128/200 |
| 3,518,992 | 7/1970 | Altounyan et al. | 128/206 |
| 3,807,400 | 4/1974 | Cocozza | 128/208 |
| 3,906,950 | 9/1975 | Cocozza | 128/206 |

*Primary Examiner*—Robert W. Michell
*Assistant Examiner*—Henry J. Recla
*Attorney, Agent, or Firm*—Smith, Harding, Earley & Follmer

[57] ABSTRACT

A nasal inhaler has a body with an open end and containing a frangible fluid containing ampul. A nozzle is mounted in the open end for movement relative to the body and the ampul. Structure responsive to the movement of the nozzle relative to the body and the ampul ruptures the ampul and releases the contained fluid.

8 Claims, 10 Drawing Figures

NASAL INHALER

BACKGROUND OF THE INVENTION

The medicinal ingredient in a nasal inhaler, for example, propylhexedrine, gradually escapes from the inhaler reducing the strength of the product and producing unwanted fumes in storage areas. This occurs despite expensive stratagems to curtail the loss of the medicament ingredient such as, for example, special sealing bands. While this problem has not heretofore been solved in inhalers, it is known to provide a medicinal ingredient for inhaling such as aromatic spirit of ammonia in a rupturable glass ampul surrounded by cotton held in place by a fabric mesh. Rupturing the ampul releases the contained liquid to the surrounding cotton and provides an inhalable ingredient. However, this structure can only be used once since there is no satisfactory way to store it for future use.

In accordance with the invention, the problem with the prior art structures is solved in that an inhaler is provided which has for all practical matters an indefinite shelf life before its initial use and which subsequently has a life equal to present inhalers employing a saturated pledget within the inhaler body which has a removable cap.

BRIEF SUMMARY OF THE INVENTION

A nasal inhaler has a body with an open end and containing a frangible fluid containing ampul. A nozzle is mounted in the open end for movement relative to the body and the ampul. Means responsive to the movement of the nozzle relative to the body and the ampul ruptures the ampul and releases the contained fluid.

DESCRIPTION OF THE PREFERRED EMBODIMENT

Figure 1:
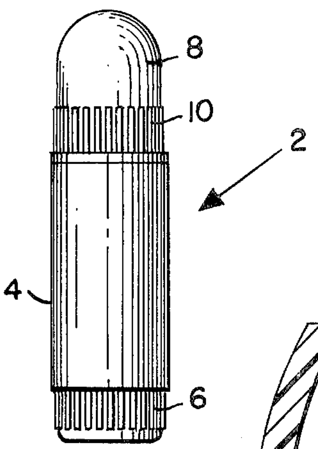
FIG. 1 is a side elevation of an inhaler in accordance with the invention.
Figure 2:
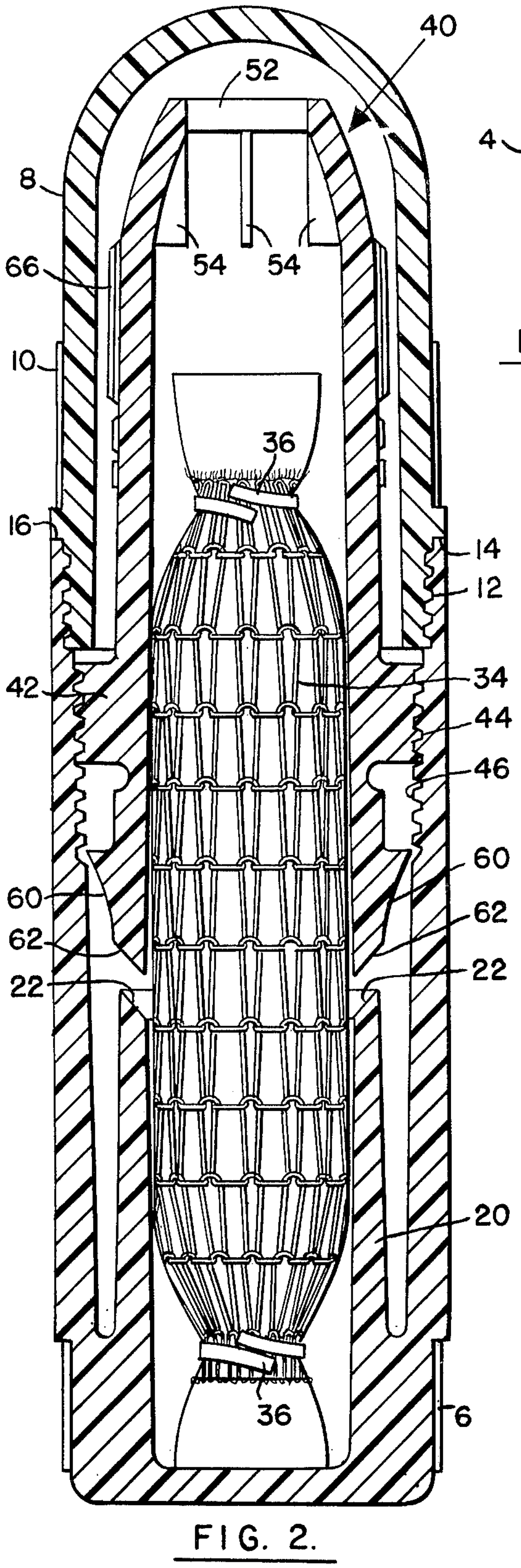
FIG. 2 is a vertical section through the inhaler of FIG. 1 showing the inhaler in the storage and shipping position.

A preferred inhaler 2 in accordance with the invention is shown in FIG. 1. Inhaler 2 has a body 4 with ridges 6 at its lower end to facilitate turning the body and a cap 8 also having ridges 10 to facilitate turning the cap. As seen in FIG. 2, cap 8 is threaded to body 4 as indicated at 12 and has a flange 14 which seals against the top 16 of body 4.

Figure 3:
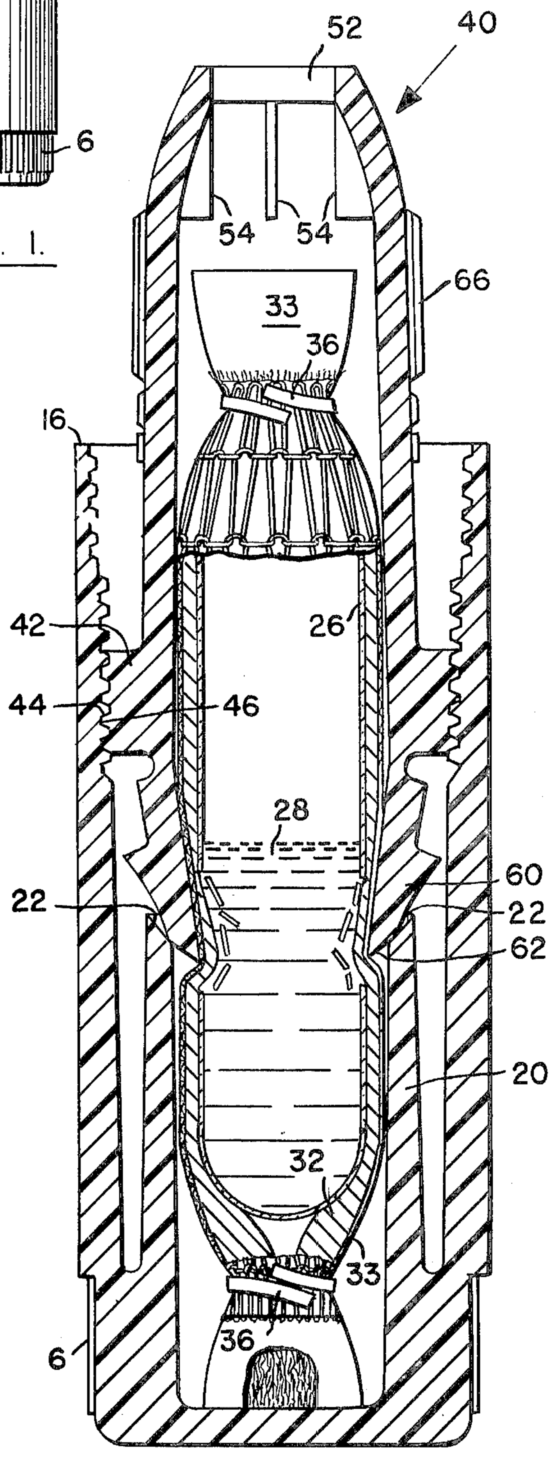
FIG. 3 is a vertical section through the inhaler of FIG. 1 with the cap removed and with the nozzle having just ruptured the ampul and before the contained liquid is absorbed by the cotton surrounding the ampul.

Body 4 in the bottom thereof has a cylindrical portion 20 the upper end of which has an inwardly sloping face 22. As best in FIG. 3 a frangible glass ampul 26 is mounted within body 4 and has its lower portion within cylindrical portion 20. Ampul 26 contains an inhalant liquid 28, for example, propylhexedrine. Ampul 26 is surrounded by an absorbent material 32, for example, cotton, and a layer of paper 33 which are held in place by a Fabric web 34 the ends of which are secured by staples 36, 36.

Figure 4:
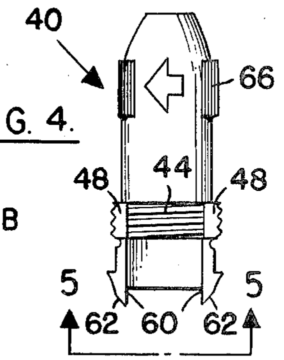
FIG. 4 is a side elevation of the nozzle of the inhaler of FIG. 1.
Figure 5:
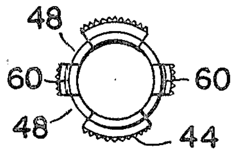
FIG. 5 is a bottom plan view of the nozzle of FIG. 4.

A nozzle 40 has an enlarged portion 42 which has threads 44 which engage threads 46 inside body 4. Threads 44 are interrupted by vertical grooves 48 (FIG. 4) to provide for the passage of air downwardly in body 4 past threads 44 and 46.

Nozzle 44 has an opening 52 through which the user inhales the inhalant of the inhaler. Integral webs 54 in the upper interior portion of nozzle 40 prevent the ampul 26 and associated elements from moving sufficiently far in the direction of opening 52 so as to block it.

A pair of opposed flexible prongs 60 depend from nozzle 40 and have inwardly sloping faces 62, 62 which are adapted to engage sloping face 22.

During storage and shipment the inhaler parts remain in the positions shown in FIG. 2. When the user is ready to use the inhaler, the cap 8 is removed by unscrewing it and the nozzle 40 is moved axially downwardly by engaging the ridged portion 66 on the exterior of the nozzle and turning it clockwise as viewed from above, the nozzle causing the faces 62 of prongs 60 to engage surface 22 which results in the prongs 60 being cammed inwardly against the web 34, sheet 33, cotton 32 and ampul 26 until 26 is shattered releasing the liquid 28 to be absorbed by the cotton 32. The user now inhales through opening 52 causing air to pass downwardly into the interior of body 4 through the grooves 48 and thence into the interior of nozzle 40 so as to pass over the cotton 32 and entrain vaporized liquid 28 which is inhaled by the user. After use, cap 8 is threaded to body 4 until flange 14 comes into sealing engagement with the top 16 of body 4.

Figure 6:
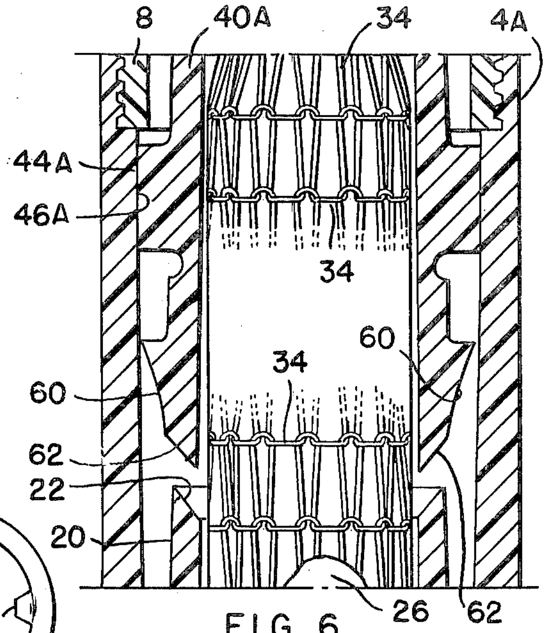
FIG. 6 is a vertical section, partially broken away, showing a modification of the inhaler of FIG. 1.
Figure 8:
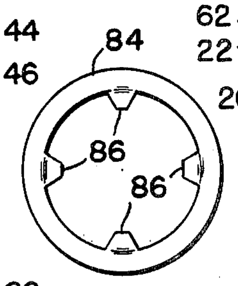
FIG. 8 is a plan view of the rupturing ring employed in the inhaler of FIG. 7.
Figure 9:
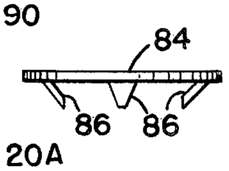
FIG. 9 is a side elevation of the rupturing ring of FIG. 8.

As shown in FIG. 6, inhaler 2 is readily modified to eliminate the threads 44 and 46 on nozzles 40 and body 4 to provide a nozzle 40A having an uninterrupted peripheral portion 44A which slidably engages an uninterrupted portion 46A of a modified body 4A. Nozzle 40A and body 4A are otherwise identical with nozzle 40 and body 4, respectively. In this case, the rupturing of ampul 26 is accomplished simply by pushing nozzle 40A into body 4A until the prongs 60 are cammed inwardly to rupture the ampul 26. The sliding fit between nozzle 40A and body 4A is sufficiently snug so that they will retain their relative positions until forced by the user's hand movements.

Figure 7:
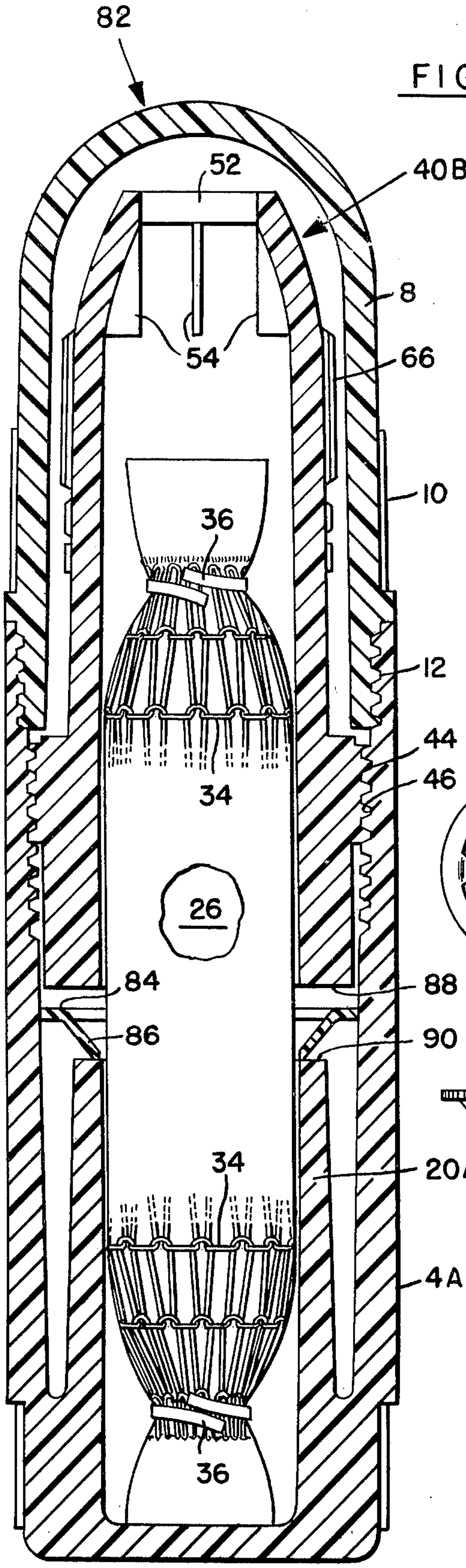
FIG. 7 is a vertical section through an alternative inhaler in accordance with the invention.

An alternative inhaler 82 is shown in FIG. 7. Inhaler 82 employs many of the parts of inhaler 2 which are therefore given the same number. Inhaler 82 has a ring 84 with integral inwardly extending arms 86 which rest on the upper end of the cylindrical portion 20A of body 4A which is the same as body 4 with the exception that the upper end 90 of cylindrical portion 20A is squared off rather than sloping. Nozzle 40B is the same as nozzle 40 with the exception that prongs 60 are eliminated and its lower end 88 is squared off in order to engage ring 84. Otherwise the inhaler 82 is the same as inhaler 2. Ring 84 is, for example, a flexible metal or plastic material of sufficient strength to rupture the ampul 26.

When it is desired to render inhaler 82 operative, nozzle 40B is turned to thread it downwardly into body 4 causing the lower end 88 to urge ring 84 downwardly which in turn causes arm 86 to be flexed upwardly by their contact with the upper end 90 of cylindrical portion 20A and urged into contact with ampul 26 to rupture it.

Figure 10:
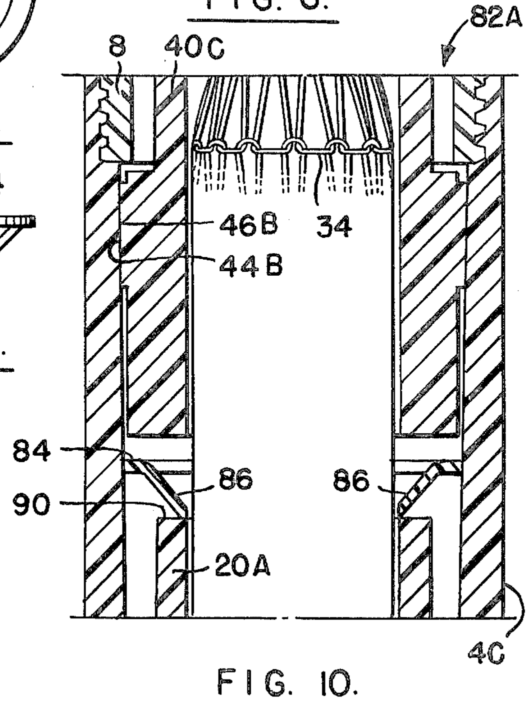
FIG. 10 is a vertical section, partially broken away, of a modification of the inhaler of FIG. 7.

As shown in FIG. 10, inhaler 82 can readily be modified to form an alternative inhaler 82A by providing a nozzle 40C which is identical to nozzle 40B but eliminating the threads to have uninterrupted portions 44B which engage in turn an uninterrupted portion 46B of a body 4C which is identical with body 4B with the exception of the elimination of the threads 46. In all other respects, the inhaler 82A is the same as inhaler 82. The operation of inhaler 82A is the same as that of inhaler 82 with the sole exception that nozzle 40C is pushed into body 4C to cause the rupturing of the ampul instead of being threaded into the body.

It will be understood that the above embodiments are illustrative and are not intended to be limiting.

I claim:

1. A nasal inhaler comprising:
- an elongated hollow body having an open end, a closed end and means to support an ampul,
- an elongated frangible fluid containing ampul supported in said body by said supporting means with its axis substantially on the axis of the body,
- an elongated one piece nozzle moveably mounted in the open end of the body for movement further into the body along the longitudinal axis of the body, means forming an air passage between the nozzle and the body for admitting air into the interior of the body, and
- means within said body including a member moveable transversely to the axis of the ampul and responsive to the movement of the nozzle further into the body for fracturing the side of the ampul and releasing the fluid.

2. A nasal inhaler in accordance with claim 1 in which the responsive means comprises:
- at least one arm integral with the inner end of the nozzle and having a cam surface on its inner end, and
- a cam fixedly mounted in the body adjacent the ampul in line with said cam surface and adapted to coact with the said cam surface to force the arm transversely to the axis of the ampul and against the ampul to rupture it on the advance of the nozzle a predetermined distance into the body.

3. The inhaler of claim 2 in which the ampul is surrounded by absorbent material.

4. The inhaler of claim 2 in which the nozzle has a thread coacting with a thread on the body for the advance of the nozzle into the body.

5. The inhaler of claim 4 in which at least one of the threads on the nozzle and the body are interrupted for providing a passage for air.

6. A nasal inhaler in accordance with claim 1 in which the responsive means comprises:
- an arm having an upper end adapted to be moved downwardly into the body by the nozzle and extending downwardly at an angle to the axis of the body with a lower portion resting on a fixed support whereby the downward movement of the nozzle against the arm causes the arm to rupture the ampul.

7. A nasal inhaler in accordance with claim 6 in which the upper end of the arm is secured to a ring movably mounted in the body adapted to be engaged by the nozzle.

8. A nasal inhaler comprising:
- an elongated hollow body having an open end, a closed end and means to support an ampul,
- an elongated frangible ampul supported in said body by said supporting means with its axis substantially on the axis of the body,
- an elongated one piece hollow nozzle overlying at least a portion of the ampul and moveably mounted in the open end of the body for movement further into the body along the longitudinal axis of the body,
- means forming an air passage between the nozzle and the body for admitting air into the interior of the body,
- a pair of opposed arms within said body, integral with the inner end of the nozzle and each having a cam surface on its inner end,
- a cam fixedly mounted in the body adjacent the ampul in line with each said cam surface and adapted to coact with the said cam surfaces to force the arms transversely to the axis of the ampul and against the ampul to fracture the side of the ampul on the advance of the nozzle a predetermined distance into the body, and
- a cap overlying the nozzle and removably connected to the body.

* * * * *